(12) United States Patent
Dumoulin et al.

(10) Patent No.: US 8,583,213 B2
(45) Date of Patent: Nov. 12, 2013

(54) COMBINED MR IMAGING AND TRACKING

(75) Inventors: Charles Dumoulin, Ballston Lake, NY (US); Patrick Gross, Munich (DE); W. Thomas Dixon, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 2001 days.

(21) Appl. No.: 11/519,562

(22) Filed: Sep. 12, 2006

(65) Prior Publication Data

US 2008/0097189 A1 Apr. 24, 2008

(51) Int. Cl.
*A61B 5/055* (2006.01)

(52) U.S. Cl.
USPC ........... 600/423; 600/410; 600/411; 600/420; 600/421; 600/422

(58) Field of Classification Search
None
See application file for complete search history.

(56) References Cited

U.S. PATENT DOCUMENTS

| | | |
|---|---|---|
| 4,680,546 A | 7/1987 | Dumoulin |
| 4,918,386 A | 4/1990 | Dumoulin et al. |
| 5,038,783 A | 8/1991 | Dumoulin |
| 5,211,165 A | 5/1993 | Dumoulin et al. |
| 5,237,277 A | 8/1993 | Lenz |
| 5,265,610 A | 11/1993 | Darrow et al. |
| 5,271,400 A | 12/1993 | Dumoulin et al. |
| 5,307,808 A | 5/1994 | Dumoulin et al. |
| 5,308,783 A | 5/1994 | Krautschneider et al. |
| 5,318,025 A | 6/1994 | Dumoulin et al. |
| 5,353,795 A | 10/1994 | Souza et al. |
| 5,365,927 A | 11/1994 | Roemer et al. |
| 5,377,678 A | 1/1995 | Dumoulin et al. |
| 5,436,562 A | 7/1995 | Dumoulin |
| 5,443,066 A | 8/1995 | Dumoulin et al. |
| 5,445,150 A | 8/1995 | Dumoulin et al. |
| 5,447,156 A | 9/1995 | Dumoulin et al. |
| 5,469,059 A | 11/1995 | Dumoulin |
| 5,548,216 A | 8/1996 | Dumoulin et al. |
| 5,577,502 A | 11/1996 | Darrow et al. |
| 5,578,924 A | 11/1996 | Dumoulin et al. |
| 5,671,739 A | 9/1997 | Darrow et al. |
| 5,713,359 A | 2/1998 | Dumoulin et al. |
| 5,715,822 A | 2/1998 | Watkins et al. |
| 6,054,858 A | 4/2000 | Dumoulin et al. |
| 6,084,411 A | 7/2000 | Giaquinto et al. |
| 6,115,485 A | 9/2000 | Dumoulin et al. |
| 6,184,684 B1 | 2/2001 | Dumoulin et al. |
| 6,198,282 B1 | 3/2001 | Dumoulin |

(Continued)

OTHER PUBLICATIONS

U.S. Appl. No. 11/248,969, filed Oct. 12, 2005, Dumoulin et al.

*Primary Examiner* — Long V. Le
*Assistant Examiner* — Bradley Impink
(74) *Attorney, Agent, or Firm* — Jason K. Klindtworth

(57) ABSTRACT

A novel method and system for employing device tracking with a magnetic resonance imaging system. In accordance with one aspect of the present technique, a method for tracking the location of a device and generating an image using magnetic resonance imaging includes applying a combined imaging and tracking pulse sequence, in the presence of a magnetic field gradient, wherein the combined imaging and tracking sequence comprising a radiofrequency excitation pulse. The method further includes collecting tracking data based on a magnetic resonance tracking signal resulting from the radiofrequency excitation pulse, wherein the magnetic resonance tracking signal is returned from a tracking coil mounted in the device. The method also includes collecting imaging data based on a magnetic resonance imaging signal resulting from the radiofrequency excitation pulse, wherein the magnetic resonance imaging signal is returned from an imaging coil.

21 Claims, 12 Drawing Sheets

(56) References Cited

U.S. PATENT DOCUMENTS

| | | |
|---|---|---|
| 6,201,987 B1 | 3/2001 | Dumoulin |
| 6,246,896 B1 | 6/2001 | Dumoulin et al. |
| 6,288,541 B1 | 9/2001 | Dumoulin |
| 6,289,233 B1 * | 9/2001 | Dumoulin et al. ............ 600/410 |
| 6,476,607 B1 * | 11/2002 | Dannels et al. ............... 324/309 |
| 6,492,814 B1 | 12/2002 | Watkins et al. |
| 6,584,337 B2 | 6/2003 | Dumoulin et al. |
| 6,687,530 B2 | 2/2004 | Dumoulin |
| 6,876,199 B2 | 4/2005 | Hardy et al. |
| 7,009,396 B2 | 3/2006 | Zhu et al. |
| 2003/0120146 A1 | 6/2003 | Dumoulin |
| 2003/0187347 A1 * | 10/2003 | Nevo et al. .................... 600/424 |
| 2004/0034297 A1 | 2/2004 | Darrow et al. |
| 2004/0171934 A1 | 9/2004 | Khan et al. |
| 2005/0054914 A1 | 3/2005 | Duerk et al. |
| 2005/0096534 A1 | 5/2005 | Zhu et al. |
| 2005/0218892 A1 | 10/2005 | Pruessmann et al. |
| 2006/0074296 A1 | 4/2006 | Dumoulin et al. |

* cited by examiner

COMBINED MR IMAGING AND TRACKING

BACKGROUND

The invention relates generally to nuclear magnetic resonance imaging ("MRI"), and more particularly to a technique for using a combined pulse sequence wherein the imaging and tracking functions share the radiofrequency ("rf") excitation pulse to allow for simultaneous MR imaging and device tracking.

MRI systems have become ubiquitous in the field of medical diagnostics. In general, MRI systems are based on the interactions among a primary magnetic field, an rf field and time varying magnetic gradient fields with nuclear spins within the subject of interest. Specific nuclear components, such as hydrogen nuclei in water molecules, have characteristic behaviors in response to external magnetic fields. The precession of spins of such nuclear components can be influenced by manipulation of the fields to obtain rf signals that can be detected, processed, and used to reconstruct a useful image.

The magnetic fields used to produce images in MRI systems include a highly uniform, static magnetic field that is produced by a primary magnet. A series of gradient fields are produced by a set of three gradient coils disposed around the subject. The gradient fields encode positions of individual volume elements or voxels in three dimensions. A radiofrequency coil is employed to produce an rf magnetic field, typically pulsed to create the required resonance signals. This rf magnetic field perturbs the spin system from its equilibrium direction, causing the spins to precess at desired phases and frequencies. During this precession, rf fields are emitted by the spins and detected by either the same transmitting rf coil, or by a separate receive-only coil. These signals are amplified, filtered, and digitized. The digitized signals are then processed using one of several possible reconstruction algorithms to reconstruct a useful image.

Many specific techniques have been developed to acquire MR images for a variety of applications. One major difference among these techniques is in the way gradient pulses and rf pulses are used to manipulate the spin systems to yield different image contrasts, signal-to-noise ratios, and resolutions. Graphically, such techniques are illustrated as "pulse sequences" in which the pulses are represented along with temporal relationships among them.

Heretofore, MRI systems have also been employed for device tracking during medical (e.g., surgical) procedures. MR tracking generally employs small tracking coils attached to the device to be tracked. During these MR tracking procedures, signals are generated throughout the patient using a large transmitting rf coil, but are detected with the small tracking coils attached to the device. In one example, locating the tracking coils may be typically accomplished by acquiring the MR signal in the presence of the applied magnetic field gradient, Fourier transforming the signal, and identifying the position of the most intense frequency-domain signal. In a manner similar to MR imaging, the gradient pulses and rf pulses used to manipulate the spin systems in MR tracking may be graphically represented as pulse sequences.

Because MR tracking utilizes much of the same hardware, instrumentation and physical phenomena as MR imaging, the device location can be overlaid onto an MR image. So that both the device location and the image may be updated during the medical procedure, the MR tracking pulse sequences are typically interleaved with the MR imaging pulse sequences. However, unlike most MR imaging methods, MR tracking can be performed rapidly (e.g., faster than 20 frames per second) over the entire three-dimensional volume of the patient. As such, the device location may be updated more frequently than the MR image. During MR tracking, it is often highly desirable that the real-time representation of the device be visualized with respect to a reference image that accurately represents the patient anatomy. In practice, this may be difficult to achieve because of patient motion and/or changes in anatomy (or function) as a result of the medical procedure.

Accordingly, there is a need for an improved technique for employing device tracking with an MRI system. Particularly, there is a need for a technique that provides for more timely synchronization between the acquisition of tracking data and imaging data.

BRIEF DESCRIPTION

The present technique provides a novel method and system for employing device tracking with an MRI system. In accordance with one embodiment of the present technique, a method is provided for tracking the location of a device and generating an image using magnetic resonance imaging. The method includes applying a combined imaging and tracking pulse sequence, in the presence of a magnetic field gradient, wherein the combined imaging and tracking sequence comprising a radiofrequency excitation pulse. The method further includes collecting tracking data based on a magnetic resonance tracking signal resulting from the radiofrequency excitation pulse, wherein the magnetic resonance tracking signal is returned from a tracking coil mounted in the device. The method also includes collecting imaging data based on a magnetic resonance imaging signal resulting from the radiofrequency excitation pulse, wherein the magnetic resonance imaging signal is returned from an imaging coil.

In accordance with another embodiment of the present technique, a method is provided for acquiring magnetic resonance imaging and tracking data. The method includes, applying a first pulse sequence, in the presence of a magnetic field gradient, wherein the first pulse sequence comprises a radiofrequency excitation pulse. The method further includes acquiring a first line of k-space data in response to the radiofrequency excitation pulse of the first pulse sequence. The method further includes applying a second pulse sequence, in the presence of a magnetic field gradient, wherein the second pulse sequence comprises a radiofrequency excitation pulse. The method further includes acquiring a second line of k-space data, in response to the radiofrequency excitation pulse of the second pulse sequence, wherein the second line of k-space data has a different orientation than the first line of k-space data.

In accordance with another embodiment of the present technique, a system for magnetic resonance imaging and tracking is provided. The system includes a scanner comprising a primary magnet coil for generating a magnetic field, a plurality of gradient coils for producing gradient fields, and a radiofrequency coil for generating radiofrequency pulses within the magnetic field. The system further includes a device comprising an operative end for positioning within the magnetic field. The system further includes a tracking coil mounted in the device for sensing magnetic resonance tracking signals, wherein the magnetic resonance tracking signals are generated in response to the radiofrequency pulses generated by the radiofrequency coil. The system also includes a control circuit configured to collect tracking data based on the magnetic resonance tracking signals, and collect imaging data based on magnetic resonance imaging signals generated in response to the radiofrequency pulses, wherein for each radiofrequency pulse a magnetic resonance tracking signal and a magnetic resonance imaging signal are collected.

In accordance with another embodiment of the present technique, a computer program, stored on a computer readable medium, for tracking the location of a device and generating an image is provided. The program is constructed and arranged to apply a combined imaging and tracking pulse sequence, wherein the combined imaging and tracking sequence comprises a radiofrequency excitation pulse. The program is further constructed and arranged to collect tracking data based on a magnetic resonance tracking signal resulting from the radiofrequency excitation pulse, wherein the magnetic resonance tracking signal is returned from a tracking coil mounted in the device. The program is also constructed and arranged to collect imaging data based on a magnetic resonance imaging signal resulting from the radiofrequency excitation pulse, wherein the magnetic resonance imaging signal is returned from an imaging coil.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
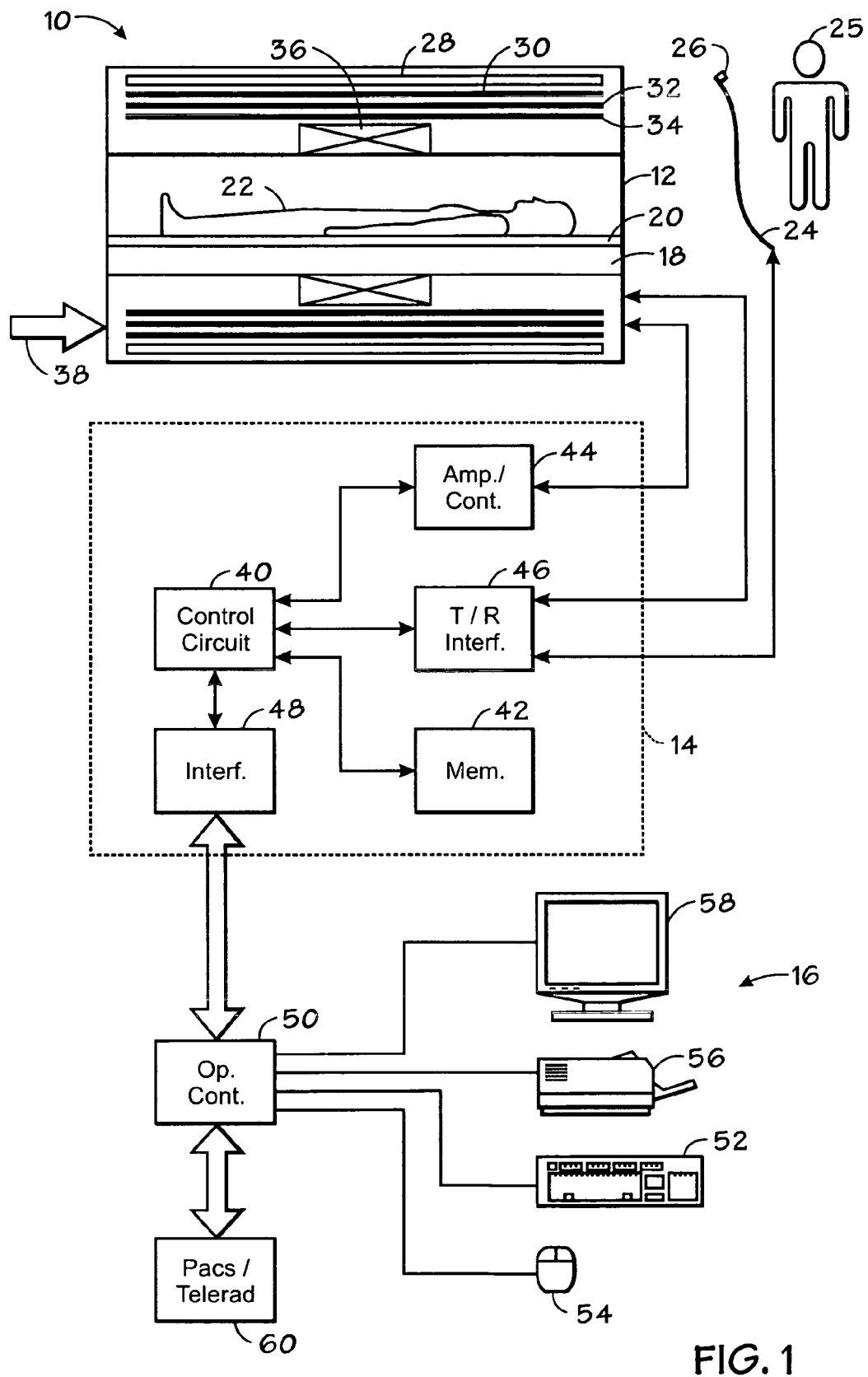
FIG. 1 is a diagrammatical representation of an MRI system for use in medical diagnostic imaging and implementing certain aspects of the present technique for simultaneous MR imaging and tracking.

Turning now to the drawings, and referring first to FIG. 1, a magnetic resonance imaging (MRI) system 10 suitable for simultaneous MR imaging and device tracking is illustrated diagrammatically as including a scanner 12, scanner control circuitry 14, and system control circuitry 16. While MRI system 10 may include any suitable MRI scanner or detector, in the illustrated embodiment the system includes a full body scanner comprising a patient bore 18 into which a table 20 may be positioned to place a patient 22 in a desired position for scanning. As illustrated in FIG. 1, a device 24 to be tracked may be inserted into patient 22 by an operator 25.

Device 24 may be any suitable device for use in a medical procedure. For example, device 24 may be a guide wire, a catheter, an endoscope, a laparoscope, a biopsy needle, an injection catheter, an injection needle, a stent delivery catheter, an ablation device, or any other similar device. Non-invasive devices, such as external coils used in tracking, are also within the scope of the present invention. As illustrated, device 24 includes an rf tracking coil 26 for receiving emissions from gyromagnetic material. Tracking coil 26 is mounted, for example, in the operative end of the device 24. Tracking coil 26 also may serve as a transmitting coil for generating radio frequency pulses for exciting the gyromagnetic material. Thus, tracking coil 26 may be coupled with driving and receiving circuitry in passive and active modes for receiving emissions from the gyromagnetic material and for applying rf excitation pulses, respectively.

Referring again to MRI system 10, scanner 12 may be of any suitable type of rating, including scanners varying from 0.5 Tesla ratings to 1.5 Tesla ratings and beyond. Scanner 12 includes a series of associated coils for producing controlled magnetic fields, for generating rf excitation pulses, and for sensing emissions from gyromagnetic material within the patient in response to such pulses. In the diagrammatical view of FIG. 1, a primary magnet coil 28 is provided for generating a primary magnetic field generally aligned with patient bore 18. A series of gradient coils 30, 32 and 34 are grouped in a coil assembly for generating controlled magnetic gradient fields during examination sequences as described more fully below. An rf coil 36 is provided for generating rf pulses for exciting the gyromagnetic material. In the embodiment illustrated in FIG. 1, rf coil 36 also serves as a receiving coil. Thus, rf coil 36 may be coupled with driving and receiving circuitry in passive and active modes for receiving emissions from the gyromagnetic material and for applying rf excitation pulses, respectively. Alternatively, various configurations of receiving coils may be provided separate from rf coil 36. Such coils may include structures specifically adapted for target anatomies, such as head coil assemblies, and so forth. Moreover, receiving coils may be provided in any suitable physical configuration, including phased array coils, and so forth.

In a present configuration, the gradient coils 30, 32 and 34 have different physical configurations adapted to their function in the imaging system 10. As will be appreciated by those skilled in the art, the coils are comprised of conductive wires, bars or plates which are wound or cut to form a coil structure which generates a gradient field upon application of controlled pulses as described below. The placement of the coils within the gradient coil assembly may be done in several different orders, but in the present embodiment, a Z-axis coil is positioned at an innermost location, and is formed generally as a solenoid-like structure which has relatively little impact on the rf magnetic field. Thus, in the illustrated embodiment, gradient coil 34 is the Z-axis solenoid coil, while coils 30 and 32 are Y-axis and X-axis coils respectively.

The coils of scanner 12 are controlled by external circuitry to generate desired fields and pulses, and to read signals from the gyromagnetic material in a controlled manner. As will be appreciated by those skilled in the art, when the material, typically bound in tissues of the patient 22, is subjected to the primary field, individual magnetic moments of the paramagnetic nuclei in the tissue partially align with the field. While a net magnetic moment is produced in the direction of the polarizing field, the randomly oriented components of the moment in a perpendicular plane generally cancel one another. During an examination sequence, an rf frequency pulse is generated at or near the Larmor frequency of the material of interest, resulting in rotation of the net aligned moment to produce a net transverse magnetic moment. This transverse magnetic moment precesses around the main magnetic field direction, emitting rf (magnetic resonance) signals. For reconstruction of the desired images, these rf signals are detected by scanner 12 and processed. For location of device 24, these rf signals are detected by rf tracking coil 26 mounted in device 24 and processed.

Gradient coils 30, 32 and 34 serve to generate precisely controlled magnetic fields, the strength of which vary over a predefined field of view, typically with positive and negative polarity. When each coil is energized with known electric current, the resulting magnetic field gradient is superimposed over the primary field and produces a desirably linear variation in the Z-axis component of the magnetic field strength across the field of view. The field varies linearly in one direction, but is homogenous in the other two. The three coils have mutually orthogonal axes for the direction of their variation, enabling a linear field gradient to be imposed in an arbitrary direction with an appropriate combination of the three gradient coils.

The pulsed gradient fields perform various functions integral to the imaging and tracking processes. For tracking, the gradient pulses are applied to produce a gradient recalled echo pulse. As discussed in more detail below, the polarity of each gradient pulse may be varied with each successive rf pulse. For imaging, some of these functions are slice selection, frequency encoding and phase encoding. These functions can be applied along the X-, Y- and Z-axis of the original physical coordinate system or in various physical directions determined by combinations of pulsed currents applied to the individual field coils.

The slice select gradient determines a slab of tissue or anatomy to be imaged in the patient. The slice select gradient field may be applied simultaneously with a frequency selective rf pulse to excite a known volume of spins within a desired slice that precess at the same frequency. The slice thickness is determined by the bandwidth of the rf pulse and the gradient strength across the field of view.

The frequency encoding gradient is also known as the readout gradient, and is usually applied in a direction perpendicular to the slice select gradient. In general, the frequency encoding gradient is applied before and during the formation of the MR echo signal resulting from the rf excitation. Spins of the gyromagnetic material under the influence of this gradient are frequency encoded according to their spatial position along the gradient field. By Fourier transformation, acquired signals may be analyzed to identify their location in the selected slice by virtue of the frequency encoding.

Finally, the phase encode gradient is generally applied before the frequency encoding gradient and after the slice select gradient. Localization of spins in the gyromagnetic material in the phase encode direction is accomplished by sequentially inducing variations in phase of the precessing protons of the material using slightly different gradient amplitudes that are sequentially applied during the data acquisition sequence. The phase encode gradient permits phase differences to be created among the spins of the material in accordance with their position in the phase encode direction. Those of ordinary skill in the art will appreciate that in three dimensional imaging an additional phase encode gradient may be applied.

As described more fully below, the present technique utilizes a combined pulse sequence (see, e.g., FIGS. 6, 8, 10 and 11), in that the imaging and tracking function share the rf frequency pulse. As will be appreciated by those skilled in the art, a great number of variations may be devised for pulse sequences employing the exemplary gradient pulse functions described above as well as other gradient pulse functions not explicitly described here. Moreover, adaptations in the pulse sequences may be made to appropriately orient both the selected slice and the frequency and phase encoding to excite the desired material and to acquire resulting MR signals for processing.

The coils of scanner 12 are controlled by scanner control circuitry 14 to generate the desired magnetic field and rf pulses. In the diagrammatical view of FIG. 1, control circuitry 14 thus includes a control circuit 40 for commanding the pulse sequences employed during the examinations, and for processing received signals. Control circuit 40 may include any suitable programmable logic device, such as a CPU or digital signal processor of a general purpose or application-specific computer. Control circuit 40 further includes memory circuitry 42, such as volatile and non-volatile memory devices for storing physical and logical axis configuration parameters, examination pulse sequence descriptions, acquired image data, programming routines, and so forth, used during the examination sequences implemented by the scanner.

Interface between the control circuit 40 and the coils of scanner 12 is managed by amplification and control circuitry 44 and by transmission and receive interface circuitry 46. Circuitry 44 includes amplifiers for each gradient field coil to supply drive current to the field coils in response to control signals from control circuit 40. Interface circuitry 46 includes additional amplification circuitry for driving rf coil 36. Moreover, where the rf coil serves both to emit the rf excitation pulses and to receive MR signals, circuitry 44 will typically include a switching device for toggling the rf coil between active or transmitting mode, and passive or receiving mode. A power supply, denoted generally by reference numeral 38 in FIG. 1, is provided for energizing the primary magnet coil 28. Finally, control circuitry 14 includes interface components 48 for exchanging configuration and image data with system control circuitry 16.

It should be noted that, while in the present description reference is made to a horizontal cylindrical bore imaging system employing a superconducting primary field magnet assembly, the present technique may be applied to various other configurations, such as scanners employing vertical fields generated by superconducting magnets, permanent magnets, electromagnets or combinations of these means. Additionally, while FIG. 1 generally illustrates an example closed MRI system, the embodiments of the present invention are applicable in open MRI systems which are designed to allow access by a physician.

System control circuitry 16 may include a wide range of devices for facilitating interface between an operator or radiologist and scanner 12 via scanner control circuitry 14. In the illustrated embodiment, for example, an operator controller 50 is provided in the form of a computer work station employing a general purpose or application-specific computer. The station also typically includes memory circuitry for storing examination pulse sequence descriptions, examination protocols, user and patient data, image data, both raw and processed, and so forth. The station may further include various interface and peripheral drivers for receiving and exchanging data with local and remote devices. In the illustrated embodiment, such devices include a conventional computer keyboard 52 and an alternative input device such as a mouse 54. A printer 56 is provided for generating hard copy output of documents and images reconstructed from the acquired data. A computer monitor 58 is provided for facilitating operator interface. In addition, system 10 may include various local and remote image access and examination control devices, represented generally by reference numeral 60 in FIG. 1. Such devices may include picture archiving and communication systems, teleradiology systems, and so forth.

Figure 2:
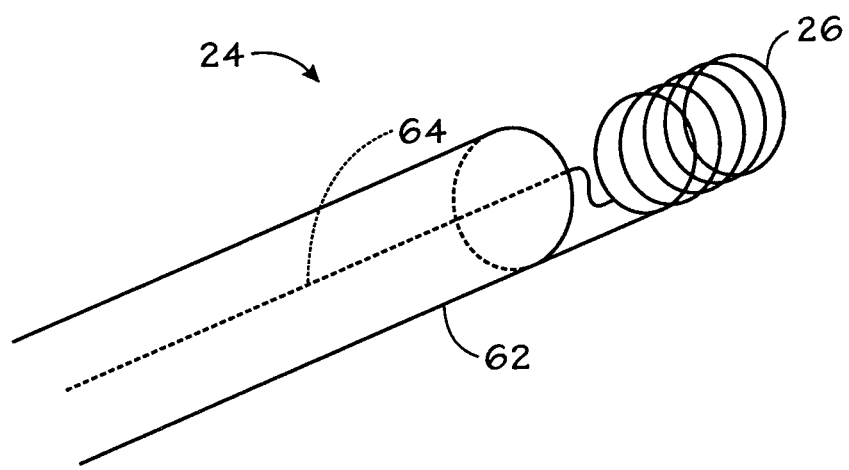
FIG. 2 is a schematic representation of an exemplary tracking coil.

Referring now to FIG. 2, the device 24 designed for insertion into a patient 22 includes a small rf tracking coil 26. As illustrated, the tracking coil 26 may be mounted in the operative end of the device 24. The device 24 may be any suitable device for use in a medical procedure. Since the tracking coil 26 is typically small in comparison to rf coil 36, its region of sensitivity is likewise small and it generally only detects MR signals from excited spins in its immediate vicinity. These MR signals are coupled to the scanner control circuitry 14 in the MRI system 10 by a pair of coaxial conductors 62, 64. These conductors are typically encased along with the tracking coil 26 in an outer shell (not shown) of the device 24.

It should be noted that, in certain embodiments, the tracking coil 26 located within device 24 performs a receive function. Alternatively, tracking coil 26 may be used to transmit rf energy and another coil, such as the rf coil 36, may be used to receive the MR response signal. In yet another embodiment, tracking coil 26 may be used to alternatively transmit and receive rf energy.

Particular tracking and imagining pulse sequences have been developed for implementation on MRI systems, such as MRI system 10 illustrated in FIG. 1 which permit acquisition of imaging data and tracking data. In general, these tracking pulse sequences are typically interleaved with the imaging pulse sequences. The imaging and the tracking data acquired utilizing these conventional pulse sequences is acquired in response to independent rf excitation pulses. As described more fully below, the present technique employs a combined pulse sequence in that the imaging and tracking functions share an rf excitation pulse. Provided below (see, e.g., FIG. 3 and FIG. 4) is a brief discussion of conventional tracking and pulse sequences that have been used to acquire tracking and imaging data, respectively.

Figure 3:
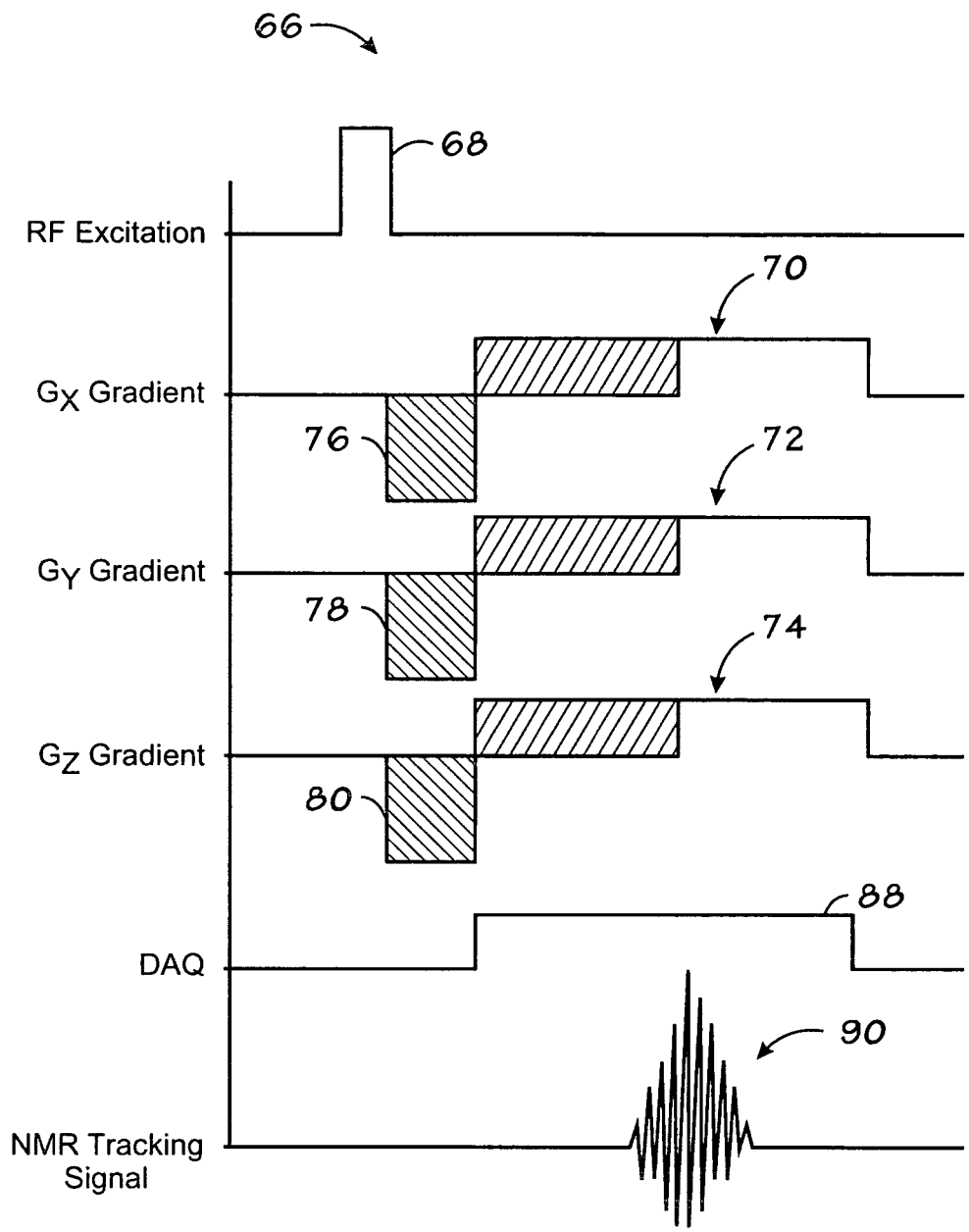
FIG. 3 is a graphical representation of an exemplary tracking pulse sequence that may be used to acquire tracking data.

By way of example, FIG. 3 illustrates a conventional tracking pulse sequence, indicated generally by reference numeral 66 that has been used developed to acquire tracking data. While many different tracking pulse sequences are used, in the example of FIG. 3, the tracking pulse sequence 66 is defined by a series of pulses applied on logical axes of the MRI system. As will be appreciated by those skilled in the art, the logical axes correspond to activities imposed on various system components, particularly the gradient and rf coils.

In the diagrammatical representation of FIG. 3, the tracking pulse sequence 66 is thus defined by an rf excitation pulse 68, a $G_x$ gradient pulse 70, a $G_y$ gradient pulse 72, a $G_z$ gradient pulse 74, and a data acquisition window 88. In general, the tracking pulse sequence 66 begins with a non-selective rf excitation pulse 68. The rf excitation pulse 68 has a selected flip angle, for example, between 10 and 60 degrees, and it produces transverse magnetization in spins located throughout the magnet bore. Three readout gradient pulses 70-74 are then applied to produce a gradient recalled MR echo signal. Each of the readout gradient pulses 70-74 is preceded by a respective de-phase lobe 76, 78 and 80. As indicated by the cross-hatching, the area of each de-phase lobe 76-80 is equal to one-half the area of the respective readout lobes 70-74. A data acquisition window 88 provides for sensing MR tracking signal 90 from the tracking coil 26.

Figure 4:
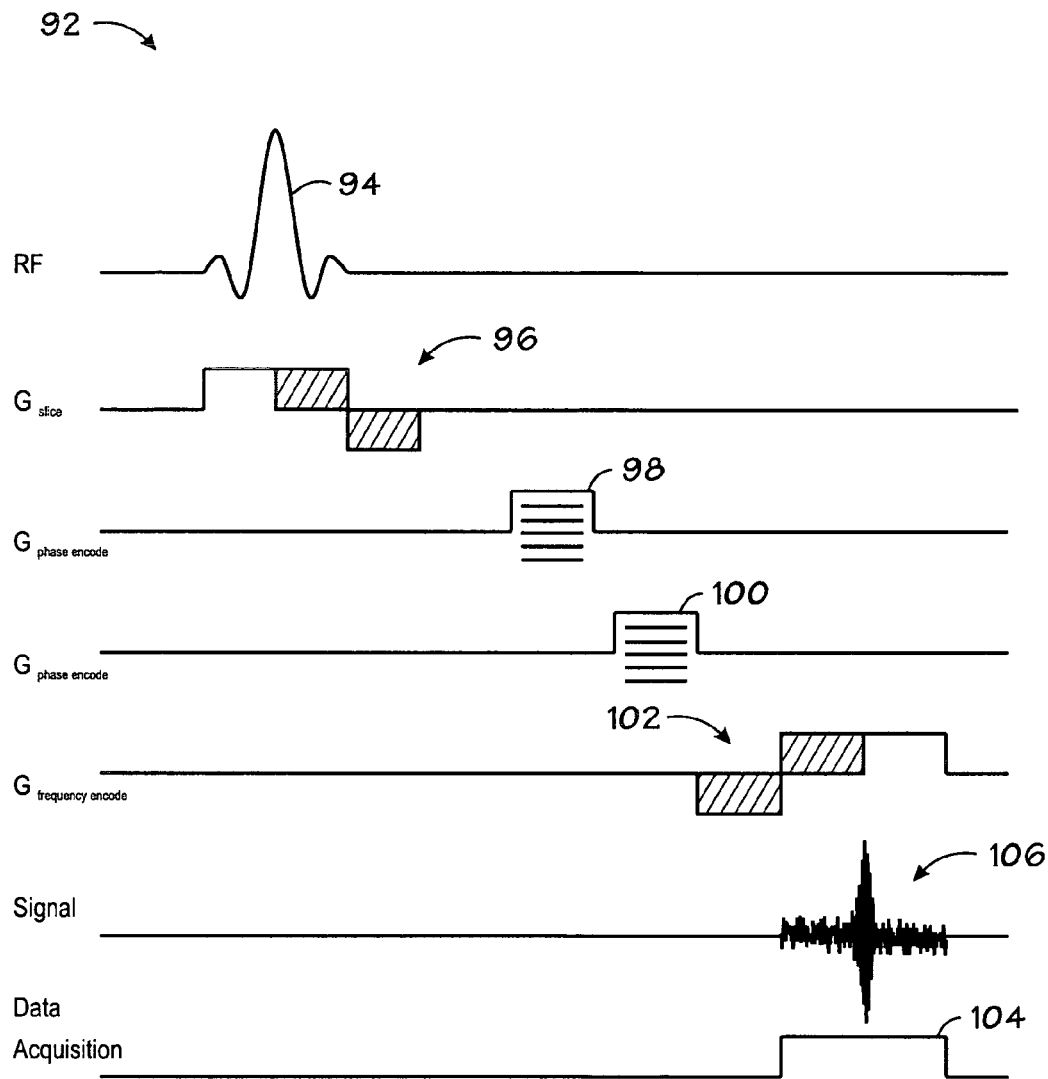
FIG. 4 is a conventional three-dimensional imaging pulse sequence that may be used to acquire imaging data.

By way of example, FIG. 4 illustrates a conventional three-dimensional imaging pulse sequence, indicated generally by reference numeral 92 that has been developed to acquire data for three dimensional imaging. While many different imaging pulse sequences are used, in the example of FIG. 4, the imaging pulse sequence 92 is defined by a series of pulses applied on logical axis of the MRI system. As illustrated, the imaging pulse sequence 92 is thus defined by an rf excitation pulse 94, a slice select gradient pulse 96, a first phase encoding gradient pulse 98, a second phase encoding gradient pulse 100, a frequency encoding gradient pulse 102, and a data acquisition window 104. In general, the imaging pulse sequence 92 begins with an rf excitation pulse 94 that is applied in the presence of the slice select gradient pulse 96 to excite gyromagnetic material in the subject. A first phase encoding gradient pulse 98 and a second phase encoding gradient pulse 100 are then generated, followed by a frequency encoding gradient pulse 102. A data acquisition window 104 provides for sensing an MR imaging signal 106 resulting from the rf excitation pulse 94 which is phase and frequency encoded.

Figure 5:
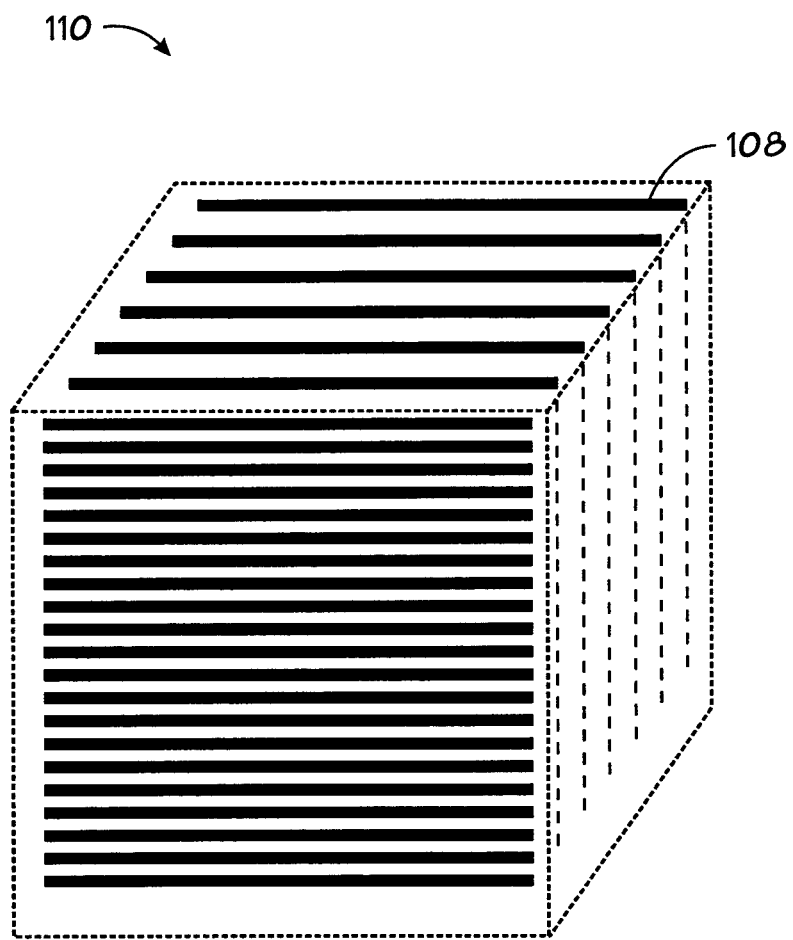
FIG. 5 is a diagrammatical representation of a conventional three-dimensional rectilinear k-space trajectory.

As will be appreciated by those skilled in the art, in conventional three-dimensional imaging, the phase and frequency encoded data sensed during data acquisition window 104 is stored as a line of data in a k-space trajectory. In other words, each application of imaging pulse sequence 92 fills one line of a k-space trajectory. As shown in FIG. 5, the acquired lines of data 108 are typically stored in the k-space trajectory, illustrated as k-space matrix 110, in a rectilinear fashion, i.e., all of the acquired lines of data 108 are stored in k-space matrix 110 in the same direction. The amplitude of the phase encoding gradient pulses 98, 100 determines the k-space location of the acquired lines of data 108 in k-space matrix 110.

For MR tracking and imaging, the conventional pulse sequence (see, e.g., FIGS. 3 and 4) discussed above are typically interleaved to acquire imaging and tracking data in response to separate rf excitation pulses. As will be appreciated by those of ordinary skill in the art, an accurate real-time representation of device 24 with respect to the MR image is highly desirable. Due to patient motion or changes in anatomy or function from the medical procedure, this may be difficult to achieve. In order to enhance synchronization between device tracking and image acquisition, the present technique utilizes combined pulse sequence wherein imaging and tracking data are acquired in response to the same rf excitation pulse.

Figure 6:
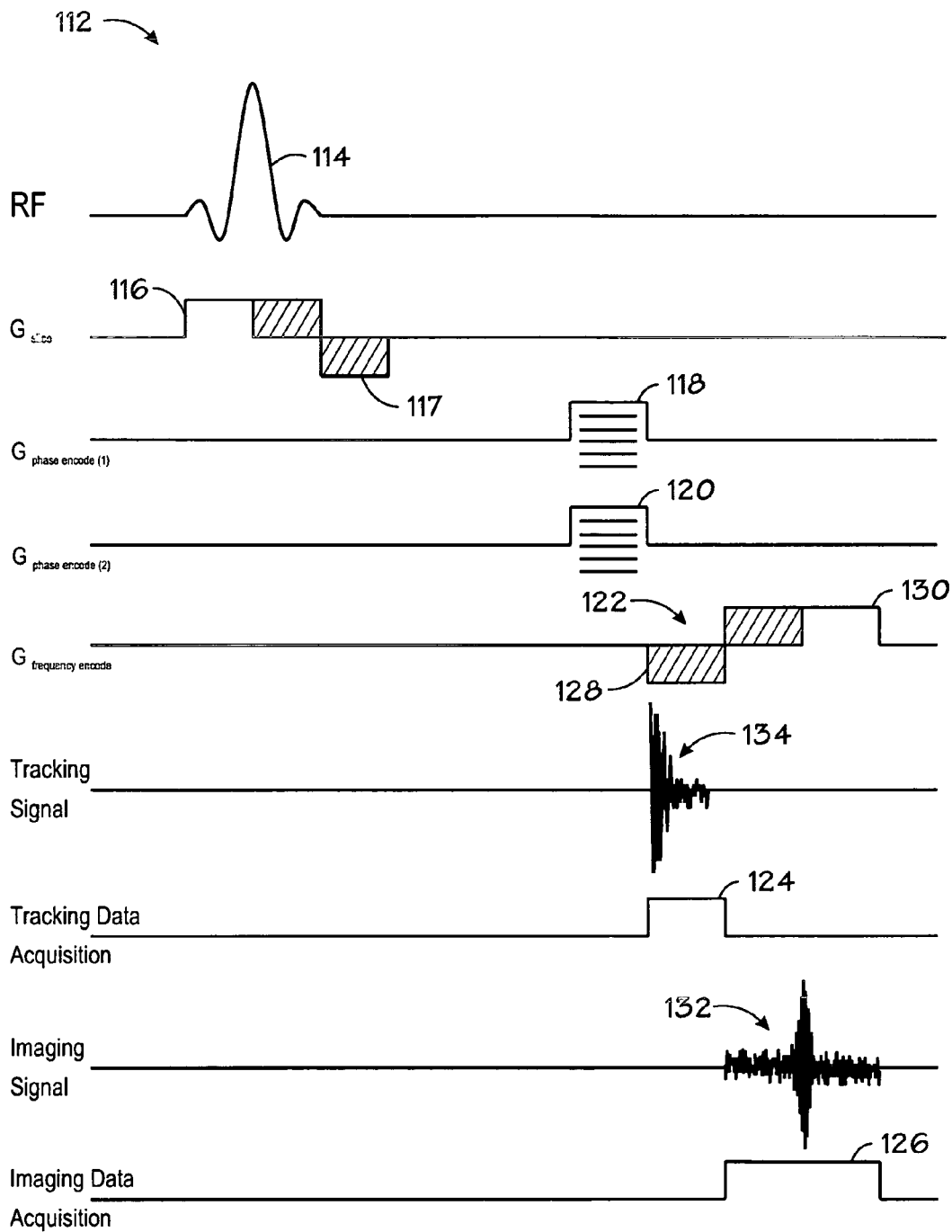
FIG. 6 is a graphical representation of a combined imaging and tracking pulse sequence in accordance with aspects of the present technique for acquiring both imaging and tracking data in response to the same rf excitation pulse.

FIG. 6 illustrates a combined pulse sequence for obtaining both imaging data and tracking data in response to the same rf excitation pulse. Using this technique, the location of device 24 and a continuously updated image may be simultaneously provided. As will be described more fully below, several alternative examples of the combined pulse sequence are available for implementing this technique.

Referring to FIG. 6, the combined pulse sequence is indicated generally by reference numeral 112. While many different combined pulse sequences may be used, in the example of FIG. 6, the combined pulse sequence 112 is generally defined by a series of rf excitation pulses and magnetic field gradient pulses appropriately timed with respect to one another. As illustrated, the combined pulse sequence 112 thus includes an rf excitation pulse 114, a slice selection gradient pulse 116, a first phase encoding gradient pulse 118, a second phase encoding gradient pulse 120, a frequency encoding gradient pulse 122, a tracking data acquisition window 124, and an imaging data acquisition window 126.

In general, the combined pulse sequence 112 begins with an rf excitation pulse 114 that is applied in the presence of a magnetic field gradient to excite a relatively large volume of patient 22. The magnetic field gradient is represented on FIG. 6 as slice select gradient pulse 116. In the present example of FIG. 6, the rf excitation pulse 114 is weakly selective in that the amplitude of the rf excitation pulse 114 and the slice selection gradient pulse 116 are chosen to excite a relatively large volume of patient 22. For example, the slice thickness may be in the range of from about 10 centimeters to about 40 centimeters. Alternatively, the rf excitation pulse 114 may be spatially non-selective so that it excites all nuclear spins within the volume of the rf coil 36. An example of an rf excitation pulse that is spatially non-selective is rf excitation pulse 68, illustrated on FIG. 3. Moreover, in the example of FIG. 6, rf excitation pulse 114 has a sin(x)/x shape to provide a square frequency response. Those of ordinary skill in the art will appreciate that a variety of different rf excitation pulses may be applied, for example, asymmetric rf pulses can be employed for more rapid excitation of the gyromagnetic material.

After the slice selection gradient pulse 116, a slice selection refocusing gradient pulse 117 is applied with a polarity opposite that of the slice selection gradient pulse 116. In the present example of FIG. 6, as indicated by the cross-hatching, the area of the slice selection refocusing gradient pulse 117 is chosen to be about one half the area of the slice selection gradient pulse 116. A first phase encoding gradient pulse 118 and a second phase encoding gradient pulse 120 are then generated, followed by a frequency encoding gradient pulse 122. While the example of FIG. 6 shows that the phase encoding gradient pulses 118, 120 and the slice selection refocusing gradient pulse 117 occur at different time, these pulses may overlap without detriment. Furthermore, frequency encoding gradient pulse 122 includes a de-phase lobe 128 and a readout lobe 130. The de-phase lobe 128 has a polarity opposite that of the readout lobe 130. In the present example of FIG. 6, as indicated by the cross-hatching, the area of de-phasing lobe 128 is equal to one half the area of the readout lobe 130.

As will be appreciated by those of ordinary skill in the art, imaging data acquisition window 126 provides for sensing imaging signals resulting from the rf excitation pulse 114 that are phase and frequency encoded. An imaging signal acquired during the imaging data acquisition window 126 is represented on FIG. 6 by reference numeral 132. Unlike conventional imaging pulse sequences, however, the present technique also provides for a tracking data acquisition window 124 during the application of the dephase lobe 128 of the frequency encoding gradient pulse 122. The tracking data acquisition window 124 provides for sensing MR tracking signals resulting from the same rf excitation pulse 114. A tracking signal acquired during the tracking data acquisition window 124 is represented on FIG. 6 by reference numeral 134. Tracking signal 134 is not acquired from rf tracking coil 36, but rather, tracking signal 134 is acquired from rf tracking coil 26 in device 24.

In a conventional three-dimensional MR imaging, the imaging pulse sequence is repeated $Y_{res}*Z_{res}$ times so that a total of $Y_{res}*Z_{res}$ lines of data (or unprocessed data) are stored in k-space, where $Y_{res}$ and $Z_{res}$ are the number of lines of k-space in the Y and Z dimensions of k-space matrix 110. For example, the imaging pulse sequence may be repeated from 128 to 256 times to acquire a sufficient amount of data for image reconstruction. The lines of data will be suitably processed and transformed for image reconstruction. As discussed above with respect to FIG. 5, for a conventional imaging pulse sequence, the acquired lines of data 108 stored in k-space matrix 110 have the same orientation. The combined pulse sequence 112 is repeated a similar number of times, but sequential applications are performed with different orientations of the frequency encoding gradient pulse 122. The orientation of the phase encoding gradient pulses 118, 120 are also changed to map the rotation applied to the frequency encoding gradient pulse 122.

While the combined pulse sequence 112 should be repeated $Y_{res}*Z_{res}$ times for image reconstruction, the location of the device 24 may be determined after a set of N combined pulse sequences has been performed, wherein N is an integer equal to 3 or greater. N should be 3 or greater because a minimum of three measurements is required to determine the three-dimensional coordinates of coil 26 in device 24. As will be appreciated by those of ordinary skill in the art, a variety of different modulation schemes for each set of N combined pulse sequences may be used to determine the location of the device. For example, the example modulation schemes provided below in Tables 1, 2, 3 and 4 modulate the polarity of the frequency encoding gradient pulse 122, thereby modulating the phase of the transverse spin magnetization created by rf excitation pulse 114.

TABLE 1

Simple Modulation of Frequency Encoding Gradient Pulse, N = 3

| Combined Pulse Sequence | $G_x$ | $G_Y$ | $G_Z$ |
|---|---|---|---|
| No. 1 | + | 0 | 0 |
| No. 2 | 0 | + | 0 |
| No. 3 | 0 | 0 | + |

TABLE 2

Hadamard Modulation of Frequency Encoding Gradient Pulse, N = 4

| Combined Pulse Sequence | $G_x$ | $G_Y$ | $G_Z$ |
|---|---|---|---|
| No. 1 | − | − | − |
| No. 2 | + | + | − |
| No. 3 | + | − | + |
| No. 4 | − | + | + |

TABLE 3

Simple Modulation of Gradient Polarities, N = 4

| Combined Pulse Sequence | $G_x$ | $G_Y$ | $G_Z$ |
|---|---|---|---|
| No. 1 | 0 | 0 | 0 |
| No. 2 | + | 0 | 0 |
| No. 3 | 0 | + | 0 |
| No. 4 | 0 | 0 | + |

TABLE 4

Simple Modulation of All Gradient Polarities, N = 6

| Combined Pulse Sequence | $G_x$ | $G_Y$ | $G_Z$ |
|---|---|---|---|
| No. 1 | − | 0 | 0 |
| No. 2 | + | 0 | 0 |

TABLE 4-continued

Simple Modulation of All Gradient Polarities, N = 6

| Combined Pulse Sequence | $G_x$ | $G_Y$ | $G_Z$ |
|---|---|---|---|
| No. 3 | 0 | − | 0 |
| No. 4 | 0 | + | 0 |
| No. 5 | 0 | 0 | − |
| No. 6 | 0 | 0 | + |

After a set of N combined pulse sequences has been performed, there should be enough tracking data to determine the location of rf tracking coil 26. As appreciated by those of ordinary skill in the art, the location of the rf tracking coil 26 may be determined using the appropriate de-multiplexing scheme for the selected modulation scheme. For example, in the modulation scheme of Table 2, Hadamard de-multiplexing may be used to determine the location of coil 26. First, the four MR tracking signals acquired in response to the four excitations are Fourier transformed to produce four corresponding projections, $P_1$, $P_2$, $P_3$, and $P_4$. Next, to determine the location of rf tracking coil 26, the location values of the signal peaks $L_1$, $L_2$, $L_3$, and $L_4$ are then combined as follows:

$$S_x = -L_1 + L_2 + L_3 - L_4 \quad (1)$$

$$S_y = -L_1 + L_2 - L_3 + L_4 \quad (2)$$

$$S_z = -L_1 - L_2 + L_3 + L_4 \quad (3)$$

wherein $S_x$, $S_y$ and $S_z$ are the x, y and z coordinates of the rf tracking coil 26. Alternatively, instead of using signal peaks in equations (1)-(3), a centroid of signal intensity in a region centered about a location of maximum signal intensity for each MR signal may be computed, as described in U.S. Pat. No. 6,687,530, the disclosure of which is incorporated herein by reference. Other suitable methodologies for determining device location also may be utilized.

As previously discussed, once the combined pulse sequence 112 has been repeated N times, the location of the rf tracking coil 26 can be determined. A device icon representing the determined location of the rf tracking coil 26 may then be displayed, for example, on computer monitor 58. In general, the device icon may be overlaid onto an image of the patient's anatomy that was reconstructed and displayed using the MR imaging system 10. The operator 25 then can use the image with the device icon overlaid thereon to guide device 24 to a desired location.

However, while the location of the rf tracking coil 26 can be determined after a set of N combined pulse sequences has been performed, there is generally insufficient data to reconstruct an image after the initial set. Accordingly, subsequent sets of excitations may be performed to acquire sufficient data to reconstruct an image. As those of ordinary skill in the art will appreciate, the subsequent sets of excitations generally may be performed with different amplitude frequency encoding gradient pulses and phase encoding gradient pulses.

Once the combined pulse sequence 112 has been repeated a sufficient number of times, $Y_{res} * Z_{res}$ times, to reconstruct an image, the acquired image data is suitably processed to reconstruct an image of the patient anatomy. This image of the patient's anatomy can be displayed, for example, on computer monitor 58. As previously described, a device icon represented the location of the rf tracking coil 26 is overlaid onto the image to enable the operator 25 to guide device 24 to a desired location.

Figure 7:
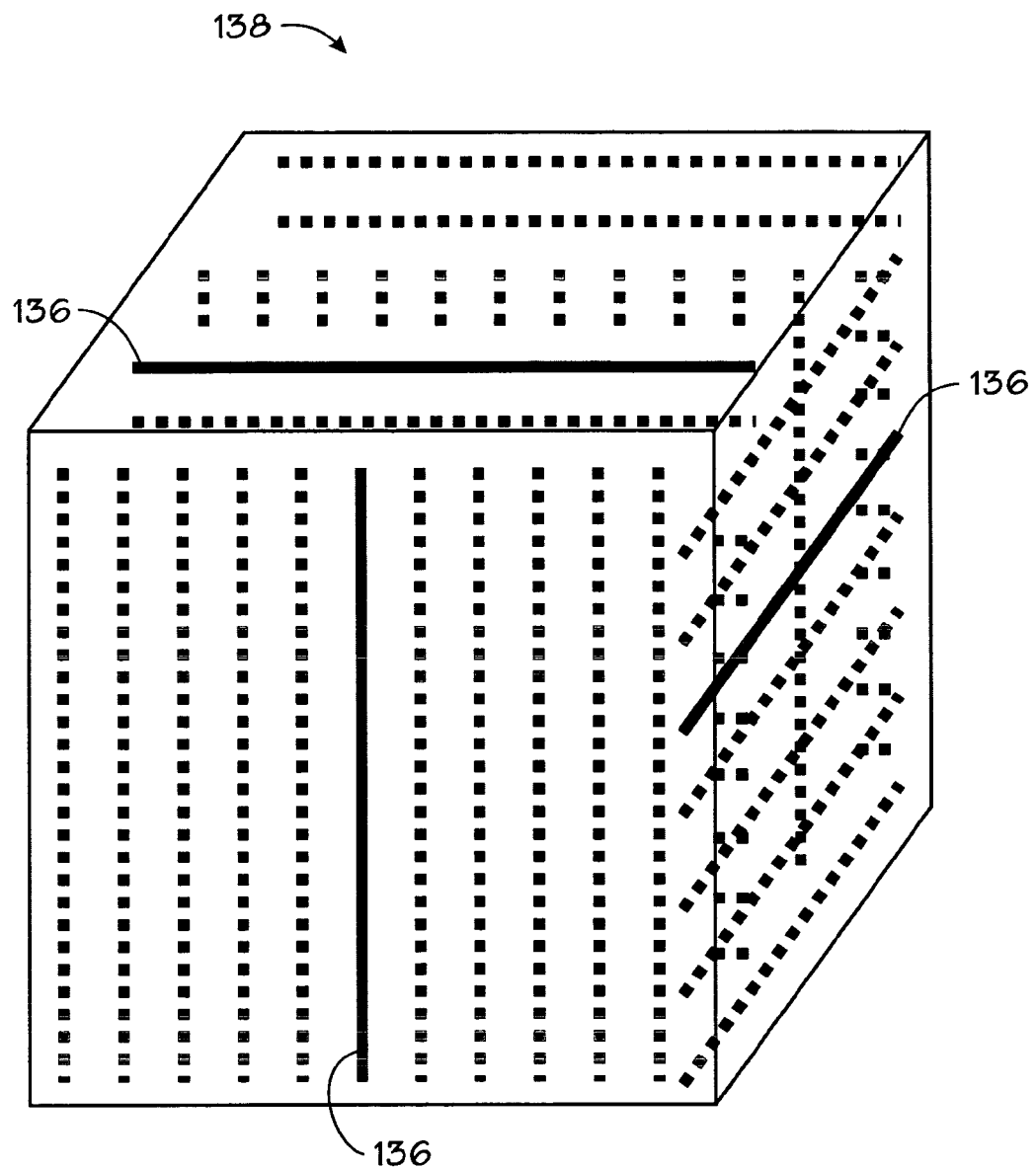
FIG. 7 is a diagrammatical representation of a k-space trajectory illustrating the acquisition of mutually orthogonal lines of data obtained through the present technique using a combined pulse sequence of the type shown in FIG. 6.

As discussed above with the respect the conventional imaging pulse sequence 92, the phase and frequency encoded data sensed during the data acquisition window is stored as a line of data in a k-space trajectory. Each application of pulse sequence 92 fills one line of a k-space trajectory. In conventional imaging pulse sequences, the acquired lines of data 108 are stored in the k-space matrix 110 in a rectilinear manner, wherein all of the lines of data 108 have the same orientation, as illustrated in FIG. 5. However, in the present technique, the gradient axis of the gradient pulses is modulated to provide the gradient polarity modulation as discussed above. Due to the modulation of the gradient axis, the k-space trajectory may be filled with a series of mutually orthogonal lines of data for the example modulation schemes shown in Tables 1, 3 and 4 above. As illustrated by FIG. 7, for the example modulation scheme of Table 1 with N=3, three mutually orthogonal lines of data 136 are sequentially acquired and stored in the k-space matrix 138. Those of ordinary skill in the art will appreciate that only a few lines of data are shown in k-space matrix 138 for clarity. Alternatively, trapezoidally oriented lines of data may be stored in the k-space matrix for the example modulation shown in Table 2.

In one embodiment of the present technique, the steps of tracking and imaging are performed continuously. In other words, the combined pulse sequence 112 may be continuously applied to the patient anatomy. When a set of N combined pulse sequences has been performed, the device location may be determined, and the device icon or image representing the device location may be displayed. Thereafter, the device icon may be continuously updated to reflect the current location of the device after each additional set of N combined pulse sequences has been performed. As such, after each subsequent set of N combined pulse sequences, a new device location may be determined, and the device icon representing the device location may be updated to reflect this current location.

Regarding image reconstruction, once a set of $Y_{res} * Z_{res}$ combined pulse sequences has been performed, a sufficient amount of image data should be available to reconstruct an image of the patient anatomy. This image may be updated with data collected in subsequent applications of the combined pulse sequence 112. In one example, the image is updated after each subsequent set of $Y_{res} * Z_{res}$ combined pulse sequences. In this example, the image data acquired in response to each subsequent set of $Y_{res} * Z_{res}$ combined pulse sequences is used to reconstruct a new image. As such, the image reconstructed from data acquired from each set of $Y_{res} * Z_{res}$ combined pulse sequences replaces the image reconstructed from the previous set of $Y_{res} * Z_{res}$ combined pulse sequences. Alternatively, the image may be updated after a set of less than $Y_{res} * Z_{res}$ combined pulse sequences. For example, image data may be acquired from repetitive applications of a set of one or more combined pulse sequences applied after the initial set of $Y_{res} * Z_{res}$ combined pulse sequences. The set of one or more combined pulse sequences generally includes fewer sequences than the set of $Y_{res} * Z_{res}$ combined pulse sequences. Next, the imaging data acquired in response to each of the sets of one or more combined pulse sequences is repetitively substituted for corresponding imaging data previously used to construct the image so that the displayed image is updated to reflect the most recently acquired data. Accordingly, an MR system using this technique will simultaneously provide three-dimensional location information for the device 24 and a continuously updated MR image of the patient anatomy.

Figure 8:
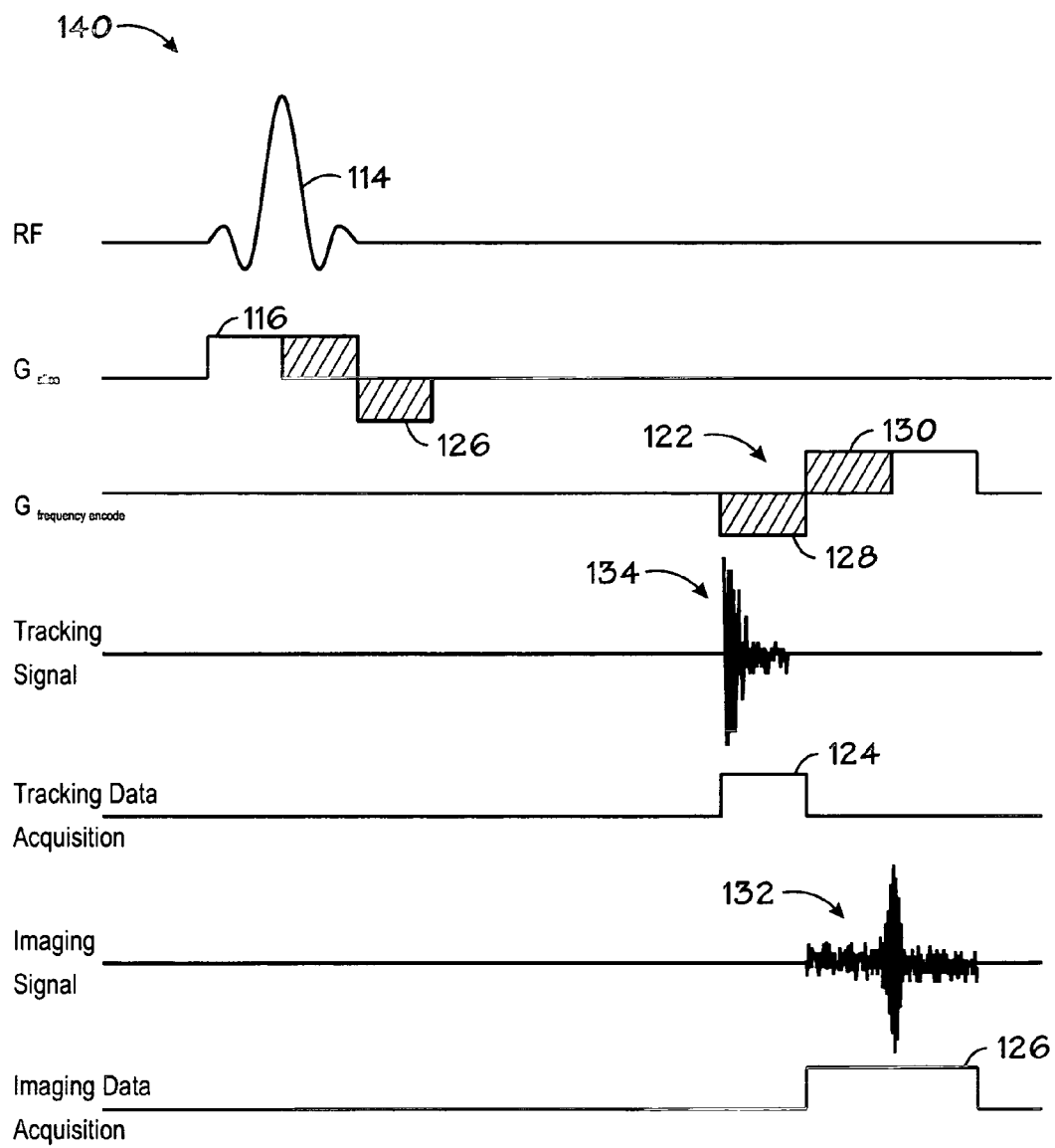
FIG. 8 is a graphical representation of an alternative combined imaging and pulse sequence similar to that of FIG. 6, but wherein a projection reconstruction technique was utilized.

As previously discussed, the present technique may be utilized with a variety of different combined imaging and tracking pulse sequences. FIG. 8 represents a variation of the combined pulse sequence illustrated in FIG. 6, which can be used to obtain both imaging data and tracking data in response to the same rf excitation pulse. However, unlike the example of FIG. 6, the second combined pulse sequence 140 uses a projection reconstruction technique, where imaging data is acquired in the absence of a phase encoding gradient pulse. A projection reconstruction technique may be used, for example, in applications desiring a minimal echo time. Rather than using a phase encoding gradient pulse, the orientation of the frequency encoding gradient pulse 122 is changed for each successive application of the second combined pulse sequence 140. Other aspects of the second combined pulse sequence 140 are generally identical to the example combined pulse sequence 112 illustrated on FIG. 6.

Figure 9:
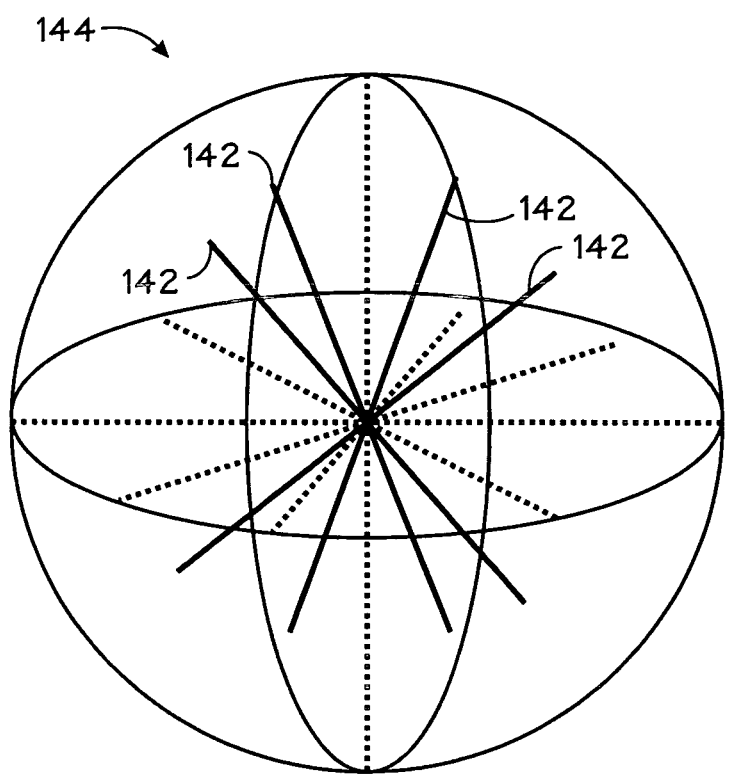
FIG. 9 is a diagrammatical representation of a "kush ball" trajectory illustrating the acquisition of data obtained through the present technique using a combined pulse sequence of the type shown in FIG. 8.

As will be appreciated by those skilled in the art, when using a three-dimensional projection-reconstruction imaging, the frequency encoded data sensed during imaging data acquisition window 126 is stored as a line of data in a k-space trajectory that is commonly referred to as a "kush ball." As illustrated by FIG. 9, for the example Hadamard modulation scheme of Table 3 with N=4, four lines of data 142 are sequentially acquired and stored in the kush-ball trajectory. Each of the lines of data 142 goes through the center of the kush-ball trajectory 144.

In the embodiments shown in FIG. 6 and FIG. 8, tracking data acquisition is shown being acquired during the application of the dephase lobe 128 of the frequency encoding gradient pulse 122. However, embodiments of the present technique may also include the acquisition of MR tracking signal 134 during application of the readout lobe 130 of the frequency encoding gradient pulse 122. Moreover, as discussed below with respect to FIG. 10 and FIG. 11, the tracking signal 134 may be acquired in one or more periods between the rf excitation pulse 114 and the end of the frequency encoding gradient pulse 122.

Figure 10:
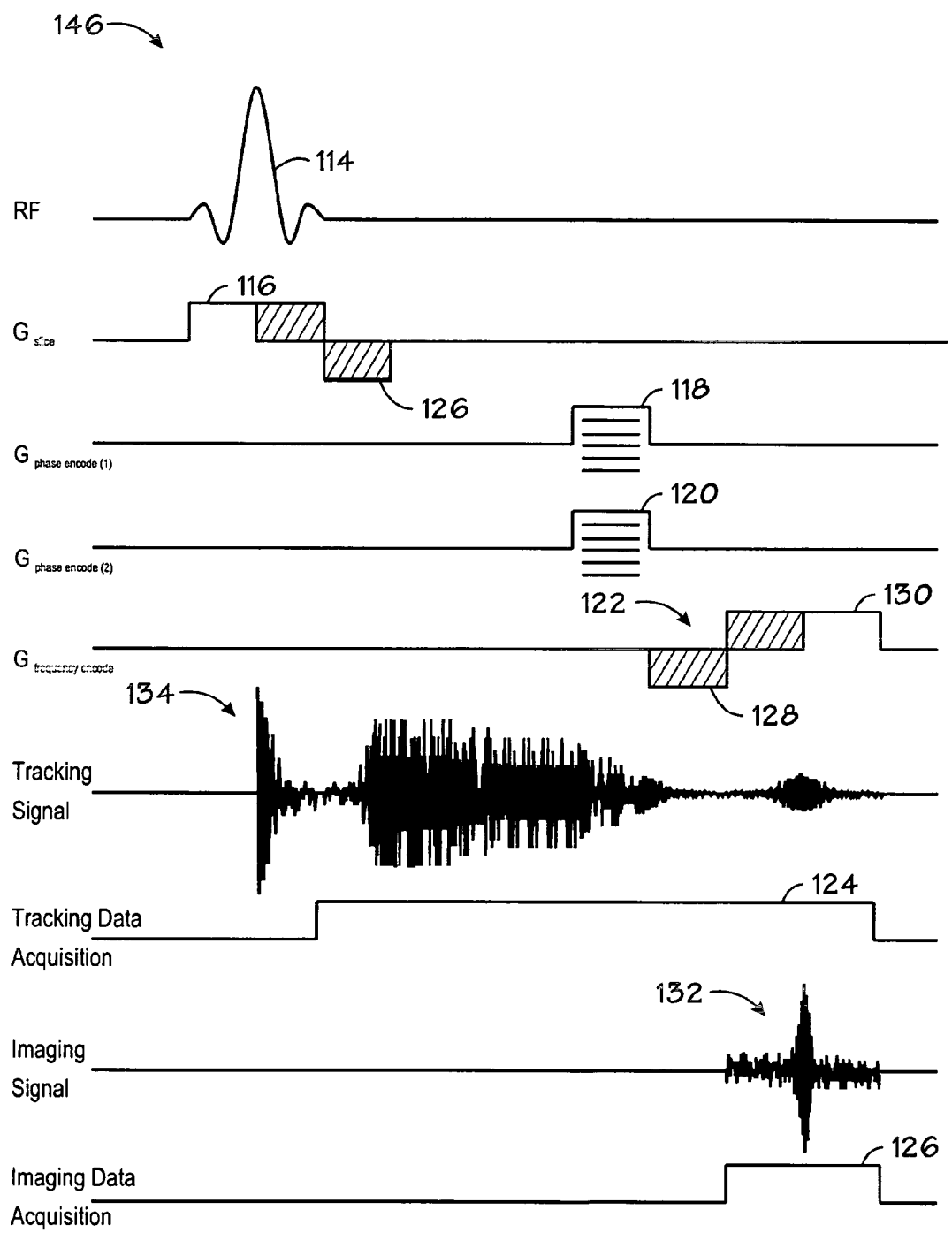
FIG. 10 is a graphical representation of an alternative combined imaging and tracking pulse sequence in accordance with aspects of the present technique.

FIG. 10 represents a further alternative combined pulse sequence in accordance with aspects of the present technique which can be used to obtain both imaging data and tracking data in response to the same rf excitation pulse. As illustrated by FIG. 10, the pulses applied during this third combined pulse sequence 146 are essentially the same as the pulses of FIG. 6. However, rather than acquiring tracking signal 134 during the dephase lobe 128 of the frequency encoding gradient pulse 122, the tracking signal 134 is acquired during tracking data acquisition window 124 between the end of the rf excitation pulse 114 and the end of the frequency encoding gradient pulse 122. While FIG. 8 illustrates one tracking data acquisition window, the tracking signal 124 may be acquired during one or more tracking data acquisition windows between the end of the rf excitation pulse 114 and the end of the frequency encoding gradient pulse 122. As discussed above, the MR signals acquired during the one or more tracking data acquisition windows will be modulated by the presence of the magnetic field gradients. In general, MR tracking signals acquired during periods of non-constant gradients, such as during gradient pulse flat tops and in between gradient pulses provide the most useful data for determining the location of tracking coil 26. However, data acquired during other periods also may be useful for determining the location of tracking coil 26.

Figure 11:
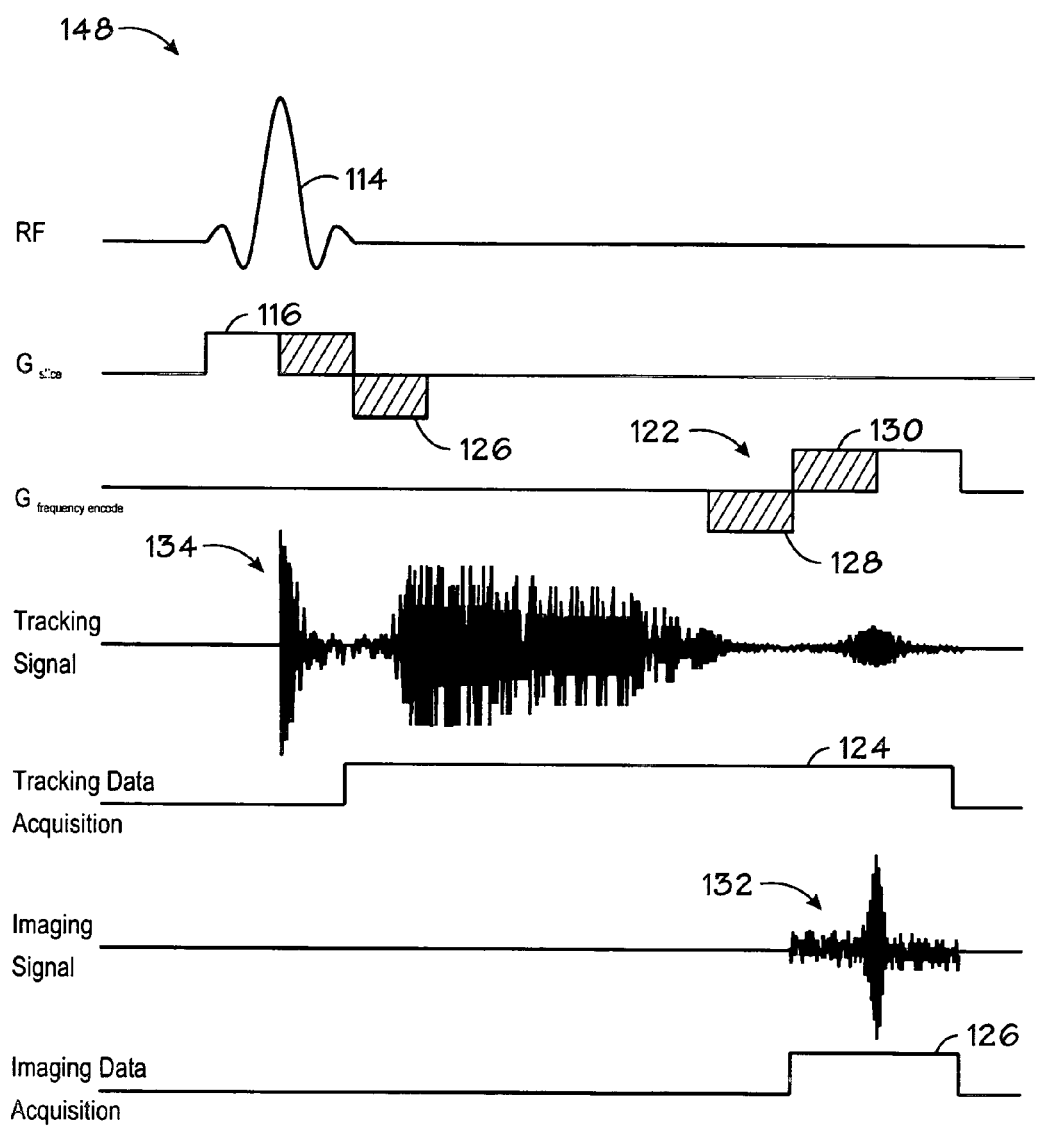
FIG. 11 is a graphical representation of an alternative combined imaging and tracking pulse sequence similar to that of FIG. 10, but wherein a projection reconstruction technique is utilized.

FIG. 11 illustrates another alternative combined pulse sequence in accordance with aspects of the present technique which can be used to obtain both imaging and tracking data in response to the same rf excitation pulse. In a manner similar to the combined pulse sequence 146 of FIG. 10, the fourth combined pulse sequence 148 of FIG. 11 acquires MR tracking signal 134 between the end of the rf excitation pulse 114 and the end of the frequency encoding pulse 122. However, unlike the example of FIG. 10, the combined pulse sequence 148 is a projection reconstruction pulse sequence where imaging data is acquired without the phase encoding gradient pulses 118, 120. Other aspects of the fourth combined pulse sequence are generally identical to the third combined pulse sequence 146 illustrated on FIG. 10.

In the embodiments shown in FIG. 10 and FIG. 11, tracking data acquisition is shown during the entire time period after the rf excitation pulse 114. As previously mentioned, the most useful tracking data is generally acquired during periods of constant gradients. As desired, the MR tracking signal 134 may be acquired during one or more tracking data acquisition windows corresponding to periods of constant gradient amplitude and no rf excitation pulse. As those of ordinary skill will appreciate, during the rf excitation pulse 114, a useful tracking signal cannot be recorded, as the signal would be dominated by the rf excitation pulse potentially damaging the receivers. However, gradient amplitudes may not be well defined during times around the gradient transitions. Moreover, in one example, to avoid periods where the gradient amplitudes are not well defined the one or more tracking data acquisition windows may not include the times around the gradient transitions.

Figure 12:
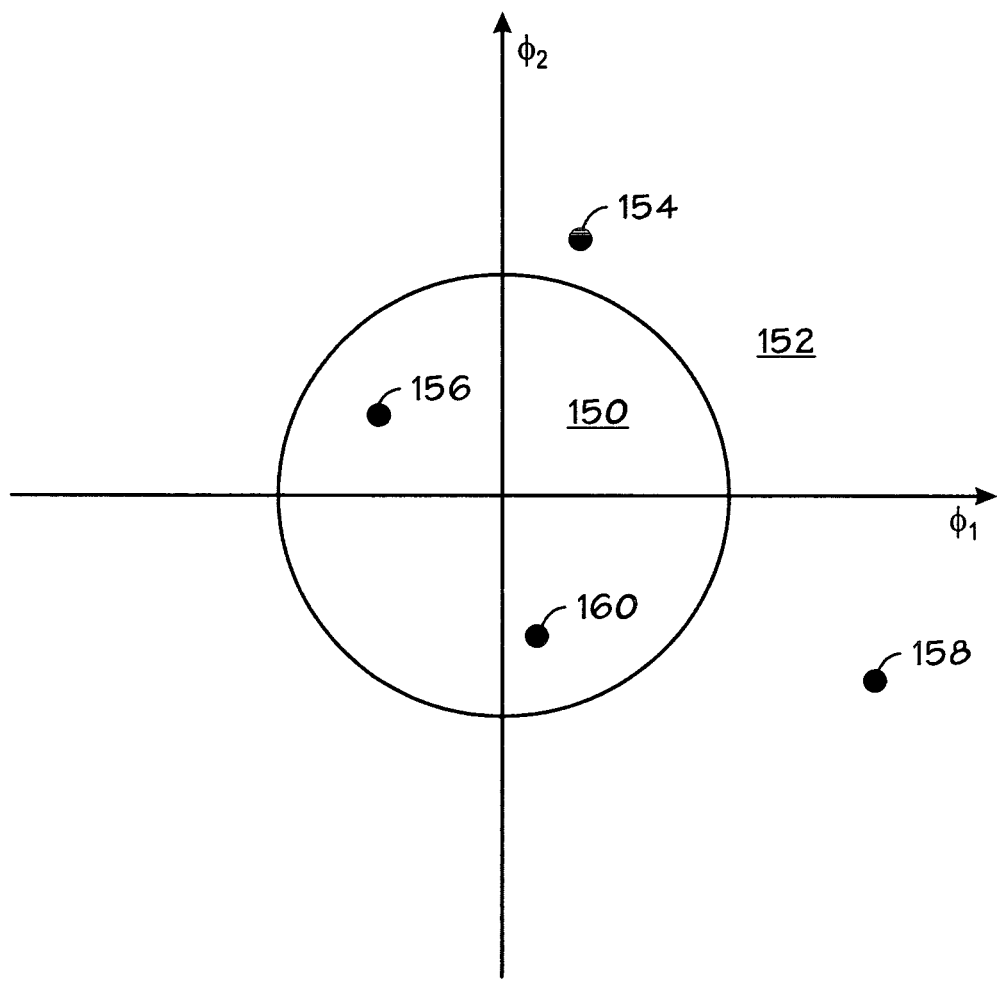
FIG. 12 is a graphical representation of a k-space trajectory illustrating lines of data acquired when alternating between peripheral k-space and central k-space.

As those of ordinary skill in the art should appreciate, the present technique may be implemented with any k-space trajectory. Implementations described above utilize a k-space matrix 138 and a "kush ball" trajectory 144 as illustrated by FIG. 7 and FIG. 9, respectively. As illustrated by FIG. 12, an example three dimensional k-space trajectory may be graphically represented with the first phase encoding gradient as the x-axis and the second phase encoding gradient as the Y-axis. It should be noted that the frequency-encoding gradient is not illustrated, as it is out-of-plane. In general, central k-space 150 may be associated with high signals while peripheral k-space 152 may be associated with high gradients (and therefore high resolution). While it may be possible to traverse k-space from the center outward, i.e., from low to high gradients, such a trajectory would impose systematic changes in the quality of the MR tracking signal. Alternatively, in the embodiment illustrated in FIG. 12, it may be desirable to alternate between central k-space 150 and peripheral k-space 150, e.g., alternate between relatively high and low gradients. Generally, alternating between high and low gradients should help to maintain the MR tracking signal quality statistically similar during the acquisition of imaging data. The numbered points shown on FIG. 12 represent acquired lines of data 154-160 in the frequency encoded direction. As illustrated, the lines of data 154-160 were acquired while alternating between peripheral k-space 150 and central k-space 152, for example, first line of data 154 was acquired in peripheral k-space 152 and then second line of data 156 was acquired in central k-space 150.

It should be noted that, while the foregoing example combined pulse sequences utilize gradient echo, other suitable pulse sequences (such as spin echo) may be utilized in accordance with the present technique. For example, periods of constant gradient amplitudes are also present during spin echo pulse sequences that may be utilized to acquire both tracking and imaging data in response to the same rf excitation pulse.

Moreover, while the foregoing the combined pulse sequences are discussed with respect to three dimensional imaging, the present technique for acquiring tracking an imaging data in response to the same rf excitation pulse may also be suitable for use with a two dimensional pulse sequence. As those of ordinary skill in the art will appreciate, MR tracking is only possible in regions of the patient 22 where spins have been excited. As previously mentioned, the volume (or slice) of the patient excited is defined by the slice gradient pulse 116 and the rf excitation pulse 114. If the device being tracked is located within the slice, the in-slice position may be determined from the tracking signal during the slice selection refocusing gradient pulse 126. However, as those of ordinary skill in the art will appreciate, if the device 24 is moved outside of the slice, no MR tracking signal is acquired. Accordingly, it should be noted that selection of a large slice is generally desirable to facilitate acquisition of the MR tracking signal 134. To allow for MR tracking during a two-dimensional pulse sequence, volume excitation based tracking may be interspersed with a combined two dimensional pulse sequence and the two dimensional plane may be adjusted to contain the tracking coil. It should be noted, however, that in some instances, this may corrupt the imaging data, for example, with slower pulse sequences.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method for tracking the location of a device and generating an image using magnetic resonance imaging, comprising:
   in the presence of a magnetic field gradient, applying a combined imaging and tracking pulse sequence, wherein the combined imaging and tracking sequence comprising a radiofrequency excitation pulse;
   collecting tracking data based on a magnetic resonance tracking signal resulting from the radiofrequency excitation pulse, wherein the magnetic resonance tracking signal is returned from a tracking coil mounted in the device; and
   collecting imaging data based on a magnetic resonance imaging signal resulting from the radiofrequency excitation pulse, wherein the magnetic resonance imaging signal is returned from an imaging coil.

2. The method of claim 1, wherein the radiofrequency excitation pulse is weakly spatially selective or spatially non-selective.

3. The method of claim 1, wherein the combined imaging and tracking pulse sequence is a spin echo pulse sequence or a gradient echo pulse sequence.

4. The method of claim 1, wherein the combined imaging and tracking pulse sequence is a projection reconstruction pulse sequence that does not include a phase encoding gradient pulse.

5. The method of claim 1, wherein the combined imaging and tracking pulse sequence further comprises a slice selection gradient pulse, a phase encoding gradient pulse, and a frequency encoding gradient pulse.

6. The method of claim 5, wherein the frequency encoding gradient pulse comprises a dephase lobe, and wherein the tracking data is collected during the dephase lobe of the frequency encoding gradient pulse.

7. The method of claim 5, wherein the tracking data are acquired during one or more periods between the radiofrequency excitation pulse and the end of the frequency encoding gradient pulse.

8. The method of claim 5, wherein the tracking data are acquired during a tracking data acquisition window between the end of the radiofrequency excitation pulse and the end of the frequency encoding gradient pulse.

9. The method of claim 5, wherein the tracking data are acquired during one or more periods of constant gradient amplitude between the radiofrequency excitation pulse and the end of the frequency encoding gradient pulse.

10. The method of claim 5, wherein the combined imaging and tracking pulse seqence further comprises a second phase encoding gradient pulse.

11. The method of claim 1, comprising repeating the steps of generating a radiofrequency excitation pulse, collecting tracking data, and collecting imaging data for a series of radiofrequency excitation pulses.

12. The method of claim 11, wherein the imaging data collected for the series of radiofrequency excitation pulses includes a corresponding series of lines of k-space data with each successive line of k-space data having a different orientation than the preceding acquired line of k-space data.

13. The method of claim 11, comprising generating an image from the image data collected in response to the series of radiofrequency excitation pulses.

14. The method of claim 11, comprising determining a position of the tracking coil from the tracking data acquired in reseponse to the series of radiofrequency excitation pulses.

15. The method of claim 14, wherein the position of the tracking coil is determined in accordance with a Hadamard de-multiplexing scheme.

16. A system for magnetic resonance imaging and tracking, comprising:
   a scanner comprising a primary magnet coil for generating a magnetic field, a plurality of gradient coils for producing gradient fields, and a radiofrequency coil for generating radiofrequency pulses within the magnetic field;
   a device comprising an operative end for positioning within the magnetic field;
   a tracking coil mounted in the device for sensing magnetic resonance tracking signals, wherein the magnetic resonance tracking signals are generated in response to the radiofrequency pulses generated by the radiofrequency coil;
   a control circuit configured to collect tracking data based on the magnetic resonance tracking signals, and collect imaging data based on magnetic resonance imaging signals generated in response to the radiofrequency pulses, wherein for each radiofrequency pulse a magnetic resonance tracking signal and a magnetic resonance imaging signal are collected.

17. The magnetic resonance tracking system of claim 16, wherein the device is a guide wire, a catheter, an endoscope, a laparoscope, a biopsy needle, an injection catheter, an injection needle, a stent delivery catheter, or an ablation device.

18. The magnetic resonance tracking system of claim 16, wherein the radiofrequency coil of the scanner senses the magnetic resonance imaging signals.

19. The magnetic resonance tracking system of claim 16, comprising a radiofrequency receiving coil for sensing the magnetic resonance imaging signals.

20. The magnetic resonance tracking system of claim 16, wherein the control circuit is further configured to generate an image from the image data, and determine a position of the tracking coil from the tracking data.

21. A computer program, stored on a computer readable medium, for tracking the location of a device and generating an image, the program constructed and arranged to:
   apply a combined imaging and tracking pulse sequence, wherein the combined imaging and tracking sequence comprising a radiofrequency excitation pulse;

collect tracking data based on a magnetic resonance tracking signal resulting from the radiofrequency excitation pulse, wherein the magnetic resonance tracking signal is returned from a tracking coil mounted in the device; and
collect imaging data based on a magnetic resonance imaging signal resulting from the radiofrequency excitation pulse, wherein the magnetic resonance imaging signal is returned from an imaging coil.

\* \* \* \* \*